United States Patent
Wink et al.

(10) Patent No.: US 7,180,976 B2
(45) Date of Patent: Feb. 20, 2007

(54) ROTATIONAL ANGIOGRAPHY BASED HYBRID 3-D RECONSTRUCTION OF CORONARY ARTERIAL STRUCTURE

(75) Inventors: Onno Wink, Denver, CO (US); Geert Richard Kemkers, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 252 days.

(21) Appl. No.: 10/516,373

(22) PCT Filed: Jun. 4, 2003

(86) PCT No.: PCT/US03/17719

§ 371 (c)(1),
(2), (4) Date: Nov. 30, 2004

(87) PCT Pub. No.: WO03/101300

PCT Pub. Date: Dec. 11, 2003

(65) Prior Publication Data

US 2005/0249327 A1    Nov. 10, 2005

Related U.S. Application Data

(60) Provisional application No. 60/385,614, filed on Jun. 4, 2002.

(51) Int. Cl.
*A61B 6/00* (2006.01)
(52) U.S. Cl. ............................. 378/8; 378/95; 378/901; 382/131; 600/428

(58) Field of Classification Search ................ 378/4, 378/8, 15, 62, 95, 901; 382/130, 131; 600/425, 600/428
See application file for complete search history.

(56) References Cited

U.S. PATENT DOCUMENTS 5,293,574 A    3/1994   Roehm et al.

(Continued)

FOREIGN PATENT DOCUMENTS

EP    1 086 652 A1    3/2001

(Continued)

OTHER PUBLICATIONS

Chen, S.J., et al.; 3-D Reconstruction of Coronary Arterial Tree to Optimize Angiographic Visualization; 2000; IEEE Trans. Med. Imaging; 19(4)318-336.

(Continued)

*Primary Examiner*—Edward J. Glick
*Assistant Examiner*—Jurie Yun
(74) *Attorney, Agent, or Firm*—Douglas B. McKnight (57) ABSTRACT

A method and apparatus of generating a hybrid three dimensional reconstruction of a vascular structure affected by periodic motion is disclosed. At least two x-ray images of the vascular structure are acquired. Indicia of the phases of periodic motion are obtained and correlated. Images from a similar phase of periodic motion are selected and a three dimensional modeled segment of a region of interest in the vascular structure is generated. A three dimensional volumetric reconstruction of a vascular structure is generated that is larger than the modeled segment. The modeled segment of interest and the volumetric reconstruction of the larger vascular structure are combined and displayed in human readable form.

25 Claims, 4 Drawing Sheets

U.S. PATENT DOCUMENTS

| | | |
|---|---|---|
| 5,588,033 A | 12/1996 | Yeung |
| 5,593,426 A | 1/1997 | Morgan et al. ............... 607/5 |
| 5,682,413 A | 10/1997 | Wong et al. |
| 5,690,106 A | 11/1997 | Bani-Hashemi et al. |
| 5,852,646 A | 12/1998 | Klotz et al. |
| 6,047,080 A | 4/2000 | Chen et al. |
| 6,125,163 A | 9/2000 | Barth et al. |
| 6,151,378 A | 11/2000 | Rasche et al. |
| 6,324,254 B1 | 11/2001 | Pflaum |
| 6,334,070 B1 | 12/2001 | Nova et al. ............... 607/5 |
| 6,366,635 B1 | 4/2002 | Op De Beek et al. |
| 6,438,417 B1 | 8/2002 | Rockwell et al. ............. 607/5 |
| 6,501,848 B1 | 12/2002 | Carroll et al. |
| 6,522,324 B1 | 2/2003 | Bosma et al. |
| 6,597,949 B1 | 7/2003 | Dhurjaty ..................... 607/5 |
| 6,639,965 B1* | 10/2003 | Hsieh et al. ................ 378/8 |
| 6,959,067 B2* | 10/2005 | Rasche et al. ............. 378/8 |
| 2003/0078500 A1* | 4/2003 | Evron et al. .............. 600/443 |
| 2003/0123718 A1* | 7/2003 | Edic et al. ................ 382/131 |
| 2003/0195567 A1 | 10/2003 | Jayne et al. ............... 607/5 |
| 2003/0212311 A1 | 11/2003 | Nova et al. .............. 600/300 |
| 2003/0233129 A1 | 12/2003 | Matos ....................... 607/5 |
| 2004/0015191 A1 | 1/2004 | Otman et al. .............. 607/5 |

FOREIGN PATENT DOCUMENTS

| | | |
|---|---|---|
| EP | 1 090 586 A2 | 4/2001 |
| EP | 1 199 031 A2 | 4/2002 |
| WO | WO 01/85030 A1 | 11/2001 |
| WO | WO 02/36011 A1 | 5/2002 |
| WO | WO 02/41780 A2 | 5/2002 |
| WO | WO 02/103639 A2 | 12/2002 |

OTHER PUBLICATIONS

Chen, S.-Y., et al.; Computer Assisted Coronary Intervention by Use of On-Line 3D Reconstructio And Optimal View Stratety; 1998; Proc. Med. Image Computing; pp. 377-385.

Dumay, A.C.M., et al.; Determination of Optimal Angiographic Viewing Angles: Basic Principles And Evaluation Study; 1994; IEEE Trans. On Med. Imag.; 13(1)13-24.

Feldkamp, L. A., et al.; Practical cone-beam algorithm; 1984; J. Opt. Soc. Am.; 1(6)612-619.

Koppe, R., et al.; Digital stereotaxy/stereotactic procedures with C-arm based Rotation-Angiography; 1996; Computer Assisted Radiology; Elsevier Pub.; pp. 17-22.

Rasche, V., et al.; ECG-gated 3D-rotational coronary angiography (3DRCA); 2002; Proc. Computer Assist. Radiology & Surgery; pp. 827-831.

Solzbach, U., et al.; Optimum Angiographic Visualization of Coronary Segments Using Computer-Aided 3D Reconstruction; 1994; Comp. & Bio. Res.; 27:178-198.

Tommasini, G., et al.; Panoramic Coronary Angiography; 1998; JACC; 31(4)871-877.

Wahle, A., et al.; Assessment of Diffuse Coronary Artery Disease by Quantitative Analysis of Coronary Morphology; 1995; IEEE Trans. On Med. Imag.; 14(2)230-241.

* cited by examiner

ROTATIONAL ANGIOGRAPHY BASED HYBRID 3-D RECONSTRUCTION OF CORONARY ARTERIAL STRUCTURE

CROSS REFERENCE TO RELATED APPLICATIONS

This application claims the benefit of U.S. provisional application Ser. No. 60/385,614 filed Jun. 4, 2002, which is incorporated herein by reference.

The present invention relates to x-ray coronary angiography and is particularly related to an apparatus that applies rotational angiography for acquiring views to generate a hybrid reconstructed and modeled representation. The present invention finds particular application in conjunction with diagnostic medical imaging for use in cardiac catheterization, diagnosis and interventional treatment and will be described with particular respect thereto.

Coronary artery disease remains a major cause of morbidity and mortality in the United States. In an effort to reduce the mortality rate, there has been a marked increase in the number of catheterizations procedures performed. In the future, the number of catheterizations is expected to increase due to recent advances in stent technology (e.g. eluting stent) and imaging capabilities.

Coronary catheterizations are generally performed using X-ray angiography. Choosing the correct stent dimensions for use during the interventional procedure is often difficult using the traditional 2D projection images due to vessel foreshortening and overlap.

Based on the specific anatomy of a specific coronary branch of clinical interest and skill of the clinician, several routine 2D single plane or biplane angiographic images from different arbitrary viewing angles are acquired in order to provide a working image for the clinician to visually estimate and derive the length and diameter of the stent to be used for subsequent intervention. Once the clinician decides upon the stent dimensions, a working view is chosen to position the x-ray system for the clinician to use during the interventional procedure. In this working view, it is desired that the vessel segment of interest is the least foreshortened and is not blocked from sight blocked from view by overlapping structures, e.g. other coronary arteries, implants or patient structures. If the working view selected based on the experience of the clinician is not as useful as desired, an alternate view is selected.

Since the patient receives a dose of contrast agent or medium and radiation for each view the clinician chooses to evaluate, this trial-and-error method of selection of appropriate viewing angles potentially exposes the patient to large amount of contrast medium (dye) and radiation, even before the actual interventional treatment of the patient begins. The contrast media presently in use places stress on a patient's kidneys and it is desirable to limit the dose amount of contrast medium to a patient. In patients that have reduced kidney function or disease, the reduction of contrast medium dose is even more important. In addition, the contrast media can harm the heart and is limited to prevent permanent damage. Likewise, it is desirable to reduce the patient's exposure to x-rays during the procedure.

In order to improve the assessment and treatment for patients relative to the 'trial-and-error' approach, several researchers have proposed various methods to construct a three-dimensional surface model of the entire arterial trees for the coronaries using two or three static 2D x-ray image acquisitions from different arbitrary viewing angles, generally needing considerable clinician experience, judgment and interaction. As a result, after obtaining the static acquisitions, the clinician has the ability to use the 2D views to generate and view a model of the entire three-dimensional coronary tree from any angle. By manipulating the model in the image the clinician is able to choose an 'optimal working view' without the use of extra radiation or dye. Modeling the entire 3-D coronary tree is still time consuming and generation of the coronary artery tree reconstruction and model are deleteriously affected by the periodic cardiac motion. In addition, the few selected views for model construction are limited to those acquired based on the skill of the clinician without the benefit of knowing the unique structure for a particular patient. The individual variation in coronary tree structure may decrease the value of one of the standard static views thereby requiring acquisition of yet another image and corresponding dose of contrast medium.

In the last few years, rotational angiography (RA) has proven to be a very accurate and effective diagnostic tool in the treatment of cerebral vessel malformations. In this approach, the C-arm rotates rapidly around the patient's head while several X-ray projections are acquired. The reconstructed cerebral vessels can be viewed from different viewing angles, while only one contrast injection is given. Due to the high reproducibility of the rotational acquisitions, the fast rotation speed, and the static nature of the cerebral vessels, the projections can be used for volumetric reconstruction providing very high detail and accuracy. In addition, the process is automated for the stationary cerebral vessel structures.

It has been demonstrated that the use of rotational arigiography for coronary vessel acquisitions yields better stenosis severity estimations and reveals lesions that were missed by only applying a few of the traditional static image acquisitions. However, straightforward volumetric reconstruction of coronary arteries has several difficulties. First, due to the beating of the heart and patient respiratory motion, present techniques only yield a rough representation of the coronaries. Given the need for accurate information regarding the dimensions of the coronary lesion for selection of the proper stent or other interventional device or procedure, it is desirable to have more precise measurements of the coronary arterial tree than possible with these rough representations. More precise information improves the diagnostic information available to clinicians in selection the optimum treatment for the patient. Although recent developments with alternative reconstruction schemes are very promising, an accurate reconstruction that can directly be used for the dimensioning of the stenoses in human subjects is not yet available or reliable enough for clinical use. Even if a suitable volumetric reconstruction could be performed, additional user interaction is needed to arrive at the correct stent dimensions.

Some efforts have been made to improve the rough reconstructions and images by attempting to compensate the rotational angiograph for periodic cardiac motion by gating the acquisition of the images to a predetermined portion of the cardiac cycle to provide a more desirable image for the reconstruction. For example, International Patent Application No. WO 02/36011 entitled "Method and Apparatus for 3D-Rotational X-Ray Imaging" describes using an x-ray imaging method for a 3D reconstruction of a coronary vascular system with a relatively long run of a scan rotation over 15 sec. to preferably 20 sec. and limited to covering 10° per second. The images are acquired using ECG cardiac triggering so that the images are obtained at the same point in the cardiac cycle.

In U.S. Pat. No. 6,324,254 entitled "Method and X-ray Device for Picking Up X-Ray Images of a Substantially Rhythmically Moving Vessel or Organ" describes an x-ray device that is slowly moved along a circular orbit at an angular velocity of less than 6° per second, during which a number of digital x-ray images are picked up, with the image pick up being triggered by the vessel motion or organ motion, e.g. an ECG device. The device rotates through 150°–200° which indicates a scan time of 25 sec. to 33 sec. The patent describes using even slower rotation rates of 2° and 0.5° which indicate a potential total scan time between 75 sec. and 400 sec. The increased scan time is necessary to obtain a sufficient number of data acquisitions for the same phase of heart cycle.

During a typical 6 sec. C-arm scan, only 30 images are obtained at the same phase of the heart cycle. Using this low number of images for the reconstruction results in poor quality of the reconstructed image. It has been indicated in the above reference that 100 such images at the same phase of the heart cycle are desired to reduce noise in the resulting reconstructed 3-D volume.

In addition, even with the improved reconstructed images using the required longer scan time, the resolution of the arterial trees still leaves room for improvement in determining the Quantitative Coronary Analysis for the dimensions of a stenosis or region of interest for treatment by the clinician. Furthermore, additional time consuming clinical user interaction is necessary in order to extract the correct dimensions of the lesion from the volumetric reconstruction.

However, due to the teaching in these disclosures requiring lengthening the rotational scan time, both of these techniques exacerbate the substantial problems of increasing patient dose for both of the contrast medium and x-ray exposure. As a result, some patients with existing kidney problems may not be able to withstand the additional required contrast medium dose for an improved reconstructed view of the coronary tree. This will reduce the quality of information available to the clinician in treatment of these patients. In addition, all patients would receive larger doses of x-radiation during these extended scan times.

Therefore it is desirable to have an angiographic procedure that will result in generating an improved hybrid three dimensional coronary arterial tree compensated for cardiac motion that provides (i) accurate modeled three dimensional representations of selected segments of the coronary arterial structure suitable for Quantitative Coronary Analysis, (ii) a hybrid modeled and volumetric reconstruction of the coronary arterial tree for selecting an improved optimal working view. It is also desirable to provide an accurate modeled representation of selected segments of the arterial tree to reduce foreshortening and overlap so that an optimal view of the lesion may be determined in a clinically practical time period for diagnostic and treatment use by the clinician during the interventional aspect of the patient's treatment.

The present invention is directed to a method and apparatus that satisfies the need to provide a clinically useful optimal view of the coronary arterial tree for coronary interventional procedures while improving the clinicians ability to obtain accurate measurements of a stenosis or lesion and still reducing the amount of time to generate clinically useful reconstructed and modeled segments, contrast agent and radiation dose to which the patient is exposed.

A method is presented to assist the clinician in planning a diagnostic or interventional procedure while the patient is already on the catheterization table. Based on several selected projections from a rotational X-ray acquisition, both a volumetric cone-beam reconstruction of the coronary tree as well as a three-dimensional surface model of the selected vessel segment of interest is generated, i.e. a partial model of the coronary arterial tree with the segment of interest. The proposed method provides the clinician with clinically accurate length and diameters of the vessel segment of interest as well as with an optimal working view. In this view, the gantry is positioned such that, for the vessel segment of interest, the foreshortening and vessel overlap are reduced during the entire heart cycle.

A method in accordance with principles of the present invention includes a method of generating a hybrid three dimensional reconstruction of a vascular structure affected by periodic motion. The method comprises placing an object affected by periodic motion to be imaged in an imaging region of an x-ray system, the object having a vascular structure and acquiring at least two x-ray images of the vascular structure. Indicia are obtained of the phases of periodic motion and correlating the indicia with each of the at least two x-ray images. At least two x-ray images are selected from a similar phase of periodic motion and a three dimensional modeled segment of a region of interest in the vascular structure is generated. The modeled segment is reconstructed using the selected x-ray images from a similar phase of periodic motion and the region of interest is only a portion of the imaged vascular structure. A three dimensional volumetric reconstruction of a vascular structure larger than the modeled segment is generated and is combined with the modeled segment of interest. The combined reconstructed vascular model and volumetric reconstruction is displayed in human readable form.

Another more limited aspect of the method applying principles of the present invention includes using x-ray images from all of the phases of the periodic motion for generating the volumetric reconstruction includes. In another limited aspect in accordance with the present invention the volumetric reconstruction is generated with gated images from a similar phase of periodic motion.

In another limited aspect of the present invention, the volumetric reconstruction includes a first portion of the vascular structure reconstructed using x-ray images from all of the phases of periodic motion and a second portion of the vascular structure reconstructed with gated images from a similar phase of the periodic motion. A more limited aspect of the method includes combining the reconstruction of both of the first portion and second portion of the vascular structure with the modeled segment of interest.

Another limited aspect in accordance with principles of the present invention is that the obtained indicia of phases of periodic motion is representative of cardiac motion and is provided by an ECG signal.

Another limited aspect in accordance with the present invention includes computation of an overlap map, the overlap map is computed by integrating all the gray values from the reconstructed volume along the rays from a virtual source that intersect the modeled segment located between the virtual source and a virtual image plane.

In yet another aspect in accordance with principles of the present invention, the step of acquiring at least two x-ray images of the vascular structure is accomplished with a rotational acquisition using a C-arm x-ray system, the rotational acquisition at an angular velocity of at least 30° per second for a scan period of at least four seconds and less than six seconds. More preferably, the angular velocity is at least 55° during the scan period.

An apparatus in accordance with principles of the present invention includes a support for an object affected by periodic motion to be imaged in an imaging region of an x-ray system. An x-ray system acquiries at least two x-ray images of the vascular structure. And ECG device obtains indicia of the phases of periodic motion affecting the object. A processor is included for correlating the indicia with each of the at least two x-ray images. A display is used for selecting at least two x-ray images from a similar phase of periodic motion. A processor is included to generate a reconstruction of a three dimensional modeled segment of a region of interest in the vascular structure, the modeled segment is reconstructed using the selected x-ray images from a similar phase of periodic motion, the region of interest only a portion of the imaged vascular structure. The processor generates a three dimensional volumetric reconstruction of a vascular structure larger than the modeled segment. In addition, the processor combines the modeled segment of interest and the volumetric reconstruction of the larger vascular structure. A display provides images of the generated reconstructions, the combined reconstructed vascular model and volumetric reconstruction as well as other maps, models etc. in human readable form.

In a more limited aspect of the present invention, the processor generates a volumetric reconstruction of a first portion of the vascular structure reconstructed using x-ray images from all of the phases of periodic motion and generates a volumetric reconstruction for a second portion of the vascular structure with gated images from a similar phase of the periodic motion.

In another aspect of an apparatus applying principles of the present invention the processor computes an overlap map of the vascular structure and modeled segment of interest, the overlap map computed by integrating all the gray values from the reconstructed volume along the rays from a virtual source that intersect the modeled segment located between the virtual source and a virtual image plane.

The claimed method and apparatus combines the complementary features of volume and surface based model reconstruction techniques. The rotational acquisition is used to minimize contrast medium and X-ray exposure. The projections that correspond to the same phase of the cardiac cycle are used to create an accurate surface-based model of the coronary segment of interest and to create an overview of the main coronary vessels.

The presented novel method includes creation of a surface model of a selected segment of interest of the cardiac arterial tree based on projections from a rotational acquisition. The method has the potential to build a model based on every projection that captures the heart at the same phase. The combination of the partial model of the segment of interest with the automatic volumetric reconstruction of the entire coronary tree using all of the acquired projections, without regard to the cardiac phase, is used for visualization of the main vessels of the coronary tree and to determine the 'optimal working view' with reduced vessel overlap and without the need to manually create a surface model of the entire coronary tree, thereby reducing reconstruction time making the process more useful for real time clinical application.

Alternatively the method may use only the acquired projections that are around the same phase of the heart that are used in generating the model. This results in a displayed coronary tree structure that appears clearer but without the benefit of a representation of vessel position as a result of coronary motion.

An apparatus and method applying principles of the present invention provides the foregoing and other features hereinafter described and particularly pointed out in the claims. The following description and accompanying drawings set forth certain illustrative embodiments applying principles of the present invention. It is to be appreciated that different embodiments applying principles of the invention may take form in various components and arrangements of components. These described embodiments being indicative of but a few of the various ways in which the principles of the invention may be employed. The drawings are only for the purpose of illustrating a preferred embodiment of an apparatus applying principles of the present invention and are not to be construed as limiting the invention.

The foregoing and other features and advantages of the present invention will become apparent to those skilled in the art to which the present invention relates upon consideration of the following detailed description of a preferred embodiment of the invention with reference to the accompanying drawings, wherein.

Figure 1:
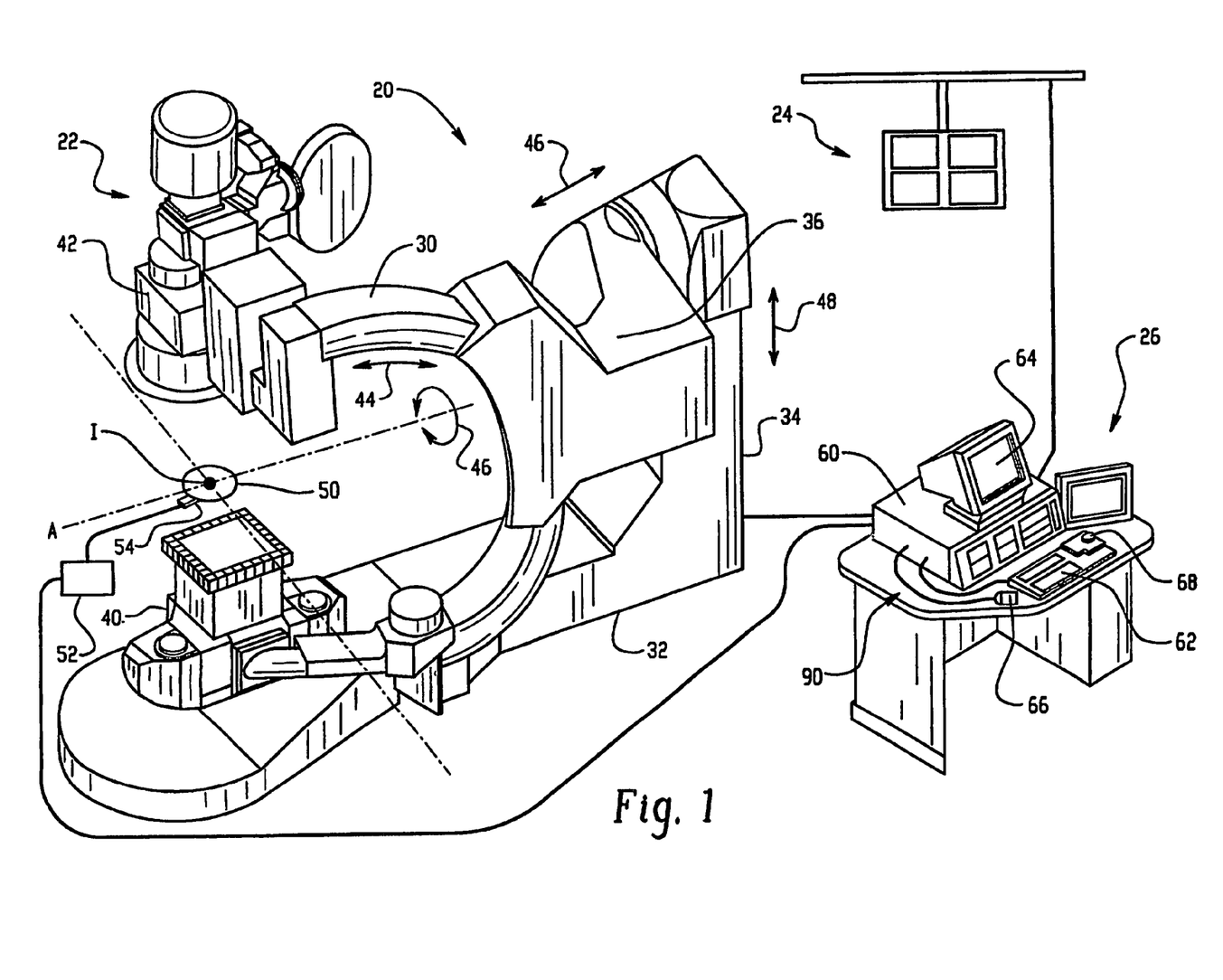
FIG. 1 is a schematic representation of an diagnostic imaging apparatus in accordance with principles of the present invention.

With reference to FIG. 1, a diagnostic imaging apparatus 20 includes an X-ray device 22, a video monitor bank 24 and diagnostic imaging control console 26. The x-ray device is a rotational angiography device comprising a C-arm system 30. A base 32 includes vertical column member 34 that supports the C-arm system 30. An arm 36 is movably attached to the vertical column member 43 for supporting a C-arm 38 that exhibits an isocenter I. The C-arm 38 has an X-ray image pickup system formed by an X-ray source 40 and an X-ray receiver 42 that are respectively mounted at the opposite ends of the C-arm 38. The X-ray receiver 42 can be an image amplifier camera system or can also be a solid-state detector. The X-ray source 40 and the X-ray receiver 42 are arranged relative to one another such that a central beam of an X-rays emanating from the X-ray source 40 is incident approximately centrally on the X-ray receiver 42.

The C-arm 38 is motor-adjustable in the direction of the double arrow 44 along its circumference. The arm 36 can be rotated as shown by double arrow 46 by motor or manually around an axis A (angulation). The C-arm is movable by motor or manually in a direction generally parallel with the axis A as shown by the double arrow 46. In addition, the C-arm 38 is vertically adjustable along the vertical column member 34 as shown by double arrow 48. Each of the moveable components are suitably monitored by known position encoders which provide the position of each component within the appropriate coordinate system for use by the imaging system control console 26. All of the motions described herein are capable of being carried out automatically by motor, or other means of causing the desired movement such as pneumatically, hydraulically etc., under the direction of the imaging system control console 26.

The C-arm X-ray system 30 is provided for the generation of 3D images of a body area of an object 50 lying on a patient support (not shown). A suitable x-ray device is a Philips Integris Allura® with a 12 inch monoplane, Philips Medical Systems an operating subsidiary of Koninklijke Philips Electronics N.V. having a principle place of business in Best, The Netherlands.

Since periodic cardiac motion causes the coronary vessels in the arterial tree to move, a reconstructed 3-D image yields only a rough representation of the coronary arterial tree. In order to improve the images used for generating the model used for the Quantitative Coronary Analysis, an ECG (electrocardiogram) device 52 is utilized to provide periodic coronary cycle information associated with each image acquired during the Rotational Acquisition. In addition the ECG information is also useful for generation of a partial volumetric reconstruction, as described below. The ECG is operatively connected with the system control console 26 and has one or more body electrodes 54 for obtaining desired periodic physiological signals.

The imaging system control console 26 coordinates the operation of the diagnostic imaging system 20. All of the control and imaging processing functions in the illustrated components and systems can be performed by known computer based systems having an operable complement of component systems such as suitable processors 60, memory and storage, input, output and data communications capabilities. A suitable workstation for the control console is an Octane system by Silicone Graphics Inc., with offices in Mountain View, Calif.

An operator interface 90 includes input and output devices suitably in communication with the control console 26 such as a keyboard 62, a touch screen monitor 64, a mouse 66, a joystick (not shown), a track ball 68 as well as other input apparatus or devices to provide operator instructions to control the imaging system and generate the model of the arterial segment of interest in the vascular structure.

Image processing and reconstruction circuitry in the control console 26 processes the output signals of the x-ray device 22 as it provides signals during an examination into an image representation. The image representation may be displayed on a video monitor, stored in computer memory, stored on tape or disk for later recall, further processed, or the like.

Figure 2:
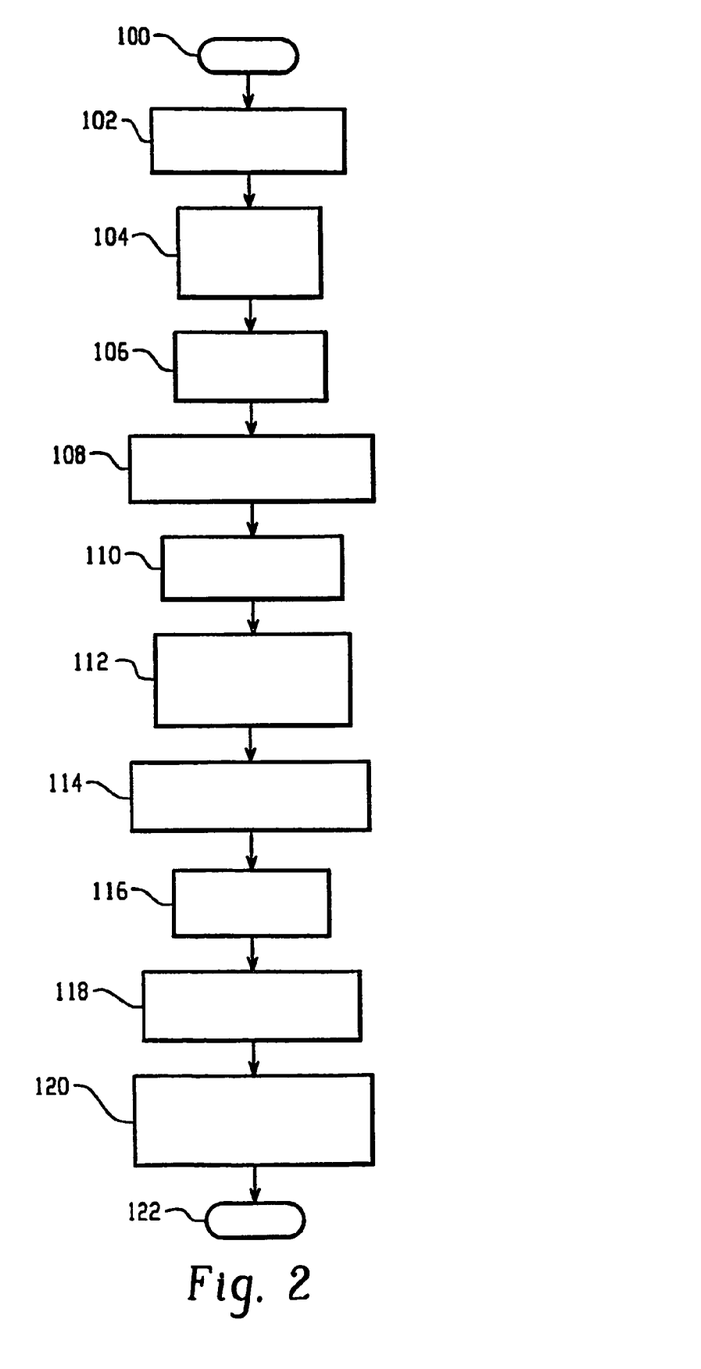
FIG. 2 is a flow diagram illustrating aspects of a method in accordance with principles of the present invention.

Turning To FIG. 2, a method in accordance with the present invention is described for use with the apparatus described above. In step 100, the diagnostic imaging apparatus is initialized and calibrated according to known methods. In step 102, the system parameters for the C-arm system such as positions of components and other conditions necessary for system operation are collected and provided to the system control 26. In step 104, the system acquires the images rotational acquisition and correlated ECG data for each acquired image. The C-arm is placed near the head-position of the table in order to perform a calibrated propeller acquisition from 120 RAO (right side of patient) to 120 LAO (left side of patient). The C-arm rotates with 55 degrees per second and acquires images at 30 frames per second during 4 seconds while the patient holds his/her breath. A total of 8–12 cc's of contrast medium (Omnipaque 350) is injected during the acquisition and started when the gantry starts rotating. This acquisition has been calibrated in step 100 and therefore, the individual projections can be corrected for the earth magnetic field and pincushion distortion and transformed to a common world coordinate system. The projections and the corresponding ECG information is stored in memory for selective recall and display on one of the monitors 24 or 64.

Next, in step 106, a sub-set of the images acquired during the rotational acquisition are displayed on the monitor bank 24 or system monitor 64 for use by the clinician. In step 108, based on the ECG signal, the projections that correspond to the same selected phase of the cardiac cycle are chosen to model the segment of the artery of interest. Usually 2 projected images from different angles are selected. The modeled segment of interest generated from acquisitions from the same portion of the cardiac cycle provide the necessary accuracy to allow the clinician to mark the displayed image and have accurate measurements generated from the model that can be used for accurate selection of the proper stent or other interventional procedure.

It is to be appreciated that the entire coronary vascular structure is not modeled. Modeling only the selected segment of interest, e.g. the stenosis or lesion which requires the improved accuracy for the Quantitative Coronary Analysis to be measured for the upcoming interventional procedure, reduces the computational time to construct the necessary maps described below such that the diagnostic process and interventional procedure may be carried out in real time with the patient in the surgical suite.

Once the desired images are selected from the rotational acquisitions, the process moves to step 110 where the model segments are generated. A suitable method for generating the model segments is described in U.S. Pat. No. 6,501,848 entitled "Method and Apparatus for Three-dimensional Reconstruction of Coronary Vessels from Angiographic Images and Analytical Techniques Applied Thereto" issued to Carroll et a., which in incorporated in its entirety by reference herein.

To construct the central axis of the modeled segment, the projections chosen above in step 108 include views in which the segment of interest is clearly visible and the angle between the two projections is around 90 degrees. Since on average five to six heartbeats are captured during the run, the user generally has a number of very desirable views from which to pick the corresponding projections with a clear view of the lesion. The central axis of the arterial segment is manually identified by the clinician by adding point pairs on the displayed image using any of the user interfaces 62, 64, 66, 68 for the system controller 26. A point in projection A yields an epipolar line in projection B, which is the ray coming from projection A towards the X-ray source. Once a point is set in one projection, the user defines the corresponding point along the epipolar line in the other projection to construct the central axis of the model. By using this 'epipolar constraint', the corresponding epipolar lines intersect and define a 3D axis point. Once the axis of the lesion is created, the clinician delineates the borders of the lumen in every projection that corresponds to the same phase of the heart in order to create and refine a surface model of the lumen. The average time to create a model for a segment of interest, once two corresponding projections are selected, is less than a minute on a SGI Octane.

Proceeding to step 112, the volumetric reconstruction is generated. An adapted version of the Feldkamp backprojection algorithm is applied to the acquired projections for the volumetric reconstruction. The projections are weighted according to the speed of time C-arm such that the projections acquired at a constant rotation speed have a higher weight than those acquired during startup and slowing down of the C-arm. If all available projections are used, the reconstruction contains information about several phases of the heart simultaneously, and is often difficult to interpret. If only those projections that correspond to the same time point in the cardiac cycle used to build the surface model, the reconstructed volume is better suited for simultaneous visualization and inspection of the artery.

The optimal view that is chosen by the clinician to perform the intervention is based on a combination of the amount of foreshortening of the segment of interest and the overlap of other coronary vascular structures. An optimal view map is so that only those C-arm gantry angles are computed that can actually be achieved for use in the interventional phase of patient treatment. In general, the cranial (toward the head of the patient) and caudal (toward the feet of the patient) angulation should not exceed 30 degrees from the anterior-posterior (AP) plane since the image intensifier contact the patient otherwise. The RAO and LAO thresholds can be set according to the capabilities of the imaging system and are currently set, for the Philips system described above, to a maximum of 60 degrees from the AP plane to avoid collision of the image intensifier with the operating table or the patient. The different values within the predefined range of angles are visualized using an interactive-color coded map. The different portions of such a map correspond to different positions e.g., quadrant or area of the map for a RAO position another corresponds to a cranial position (bottom with caudal). The clinician has the opportunity to inspect the different viewing angles in real time by clicking at a position in the map displayed on the monitor 64 and to toggle between the different maps. The amount of foreshortening and overlap are given in the lower right hand side of the display.

In step 114, the foreshortening map is computed by comparing the length of the modeled segment to the projected length of this segment as if it were viewed from a typical viewpoint as defined by the range of angles in the map.

Next, in step 116, a novel method of computing the overlap map is carried out by the control console 26. Although the volumetric reconstruction of all the acquired projections yields only a rough representation of the coronaries, it does provide useful information such as the location of the vessels and other objects (e.g. the spine, ribs and pacemaker or ECG-leads) during all the phases of the heart.

Figure 3:
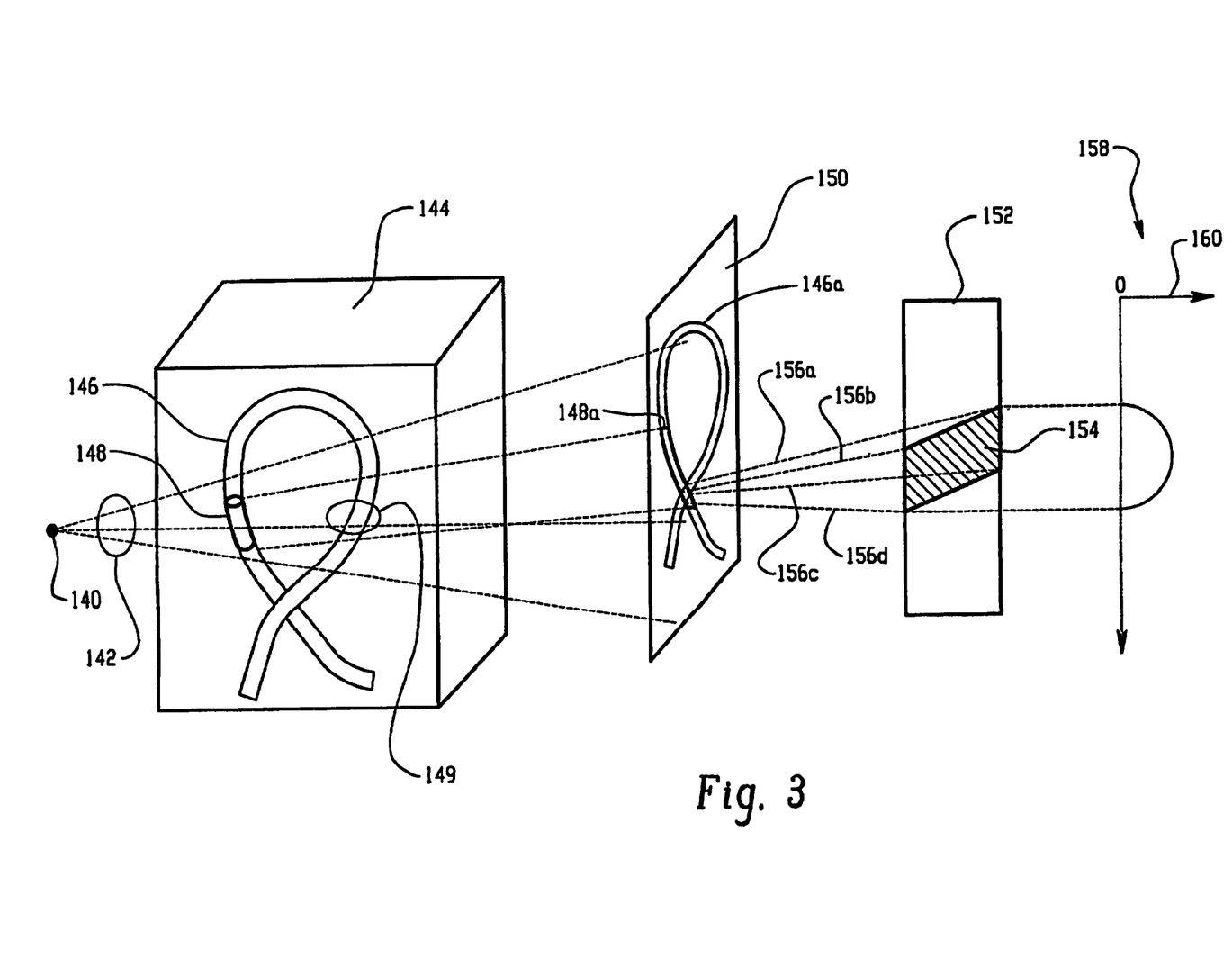
FIG. 3 is a schematic representation of a process in accordance with principles of the present invention to generate an overlap map.

Turning now to FIG. 3, a simplified example is schematically illustrated of the novel method, in accordance with the present invention, for determining the overlap map. The overlap map is computed by taking the integral of all the gray values from the reconstructed volume along the rays that intersect the modeled segment. A virtual x-ray source 140 has a plurality of rays 142 corresponding to a volumetric reconstruction 144. A lumen 146 is represented in the reconstruction with a modeled segment 148 of interest such as a stenosis or lesion. An overlap area 149 is where another portion of the lumen or another structure intercepts a ray that has also passed through the modeled segment 148. A planar representation of the sum of gray values 150 has a corresponding lumen representation 146a of the lumen 146 and its model segment 148 shown as 148a in representation 150. An illustration of the sum of gray values on the model segment 152 is shown to include an area 154 defining the overlap area of the modeled segment and the lumen. The four dashed lines 156a,b,c,d schematically illustrate a visualization sum of gray values along a ray that are projected on the model. This represents the concept of the overlap of the vascular structure creating a distribution which provides the representation in the graph 158 with intensity illustrated on the axis 160. The graph 158 illustrates the intensities (=sum of gray values along the ray) over a single line. The final value is the integral or sum of all the sum of gray values in the projection of the modeled segment. This gray value integration technique is efficiently implemented in OpenGL using space-leaping techniques and the Stencil Buffer in combination with the special purpose graphics hardware of the SGI Octane.

Next, in step 118, the optimal view map can he constructed by taking a weighted sum of normalized values of the foreshortening map and overlap map. For a practical implementation and efficient computation, the vessel overlap is generally estimated for gantry angles where the vessel foreshortening has been reduced or minimized in order to obtain the resultant optimal working view.

In step 120, the combined reconstructed image including the volumetric reconstruction and modeled segment, the optimal view map and system parameters to locate the gantry for a selected optimum view are displayed on monitors in the monitor bank 24 or control console 26. The process terminates in step 122.

Figure 4:
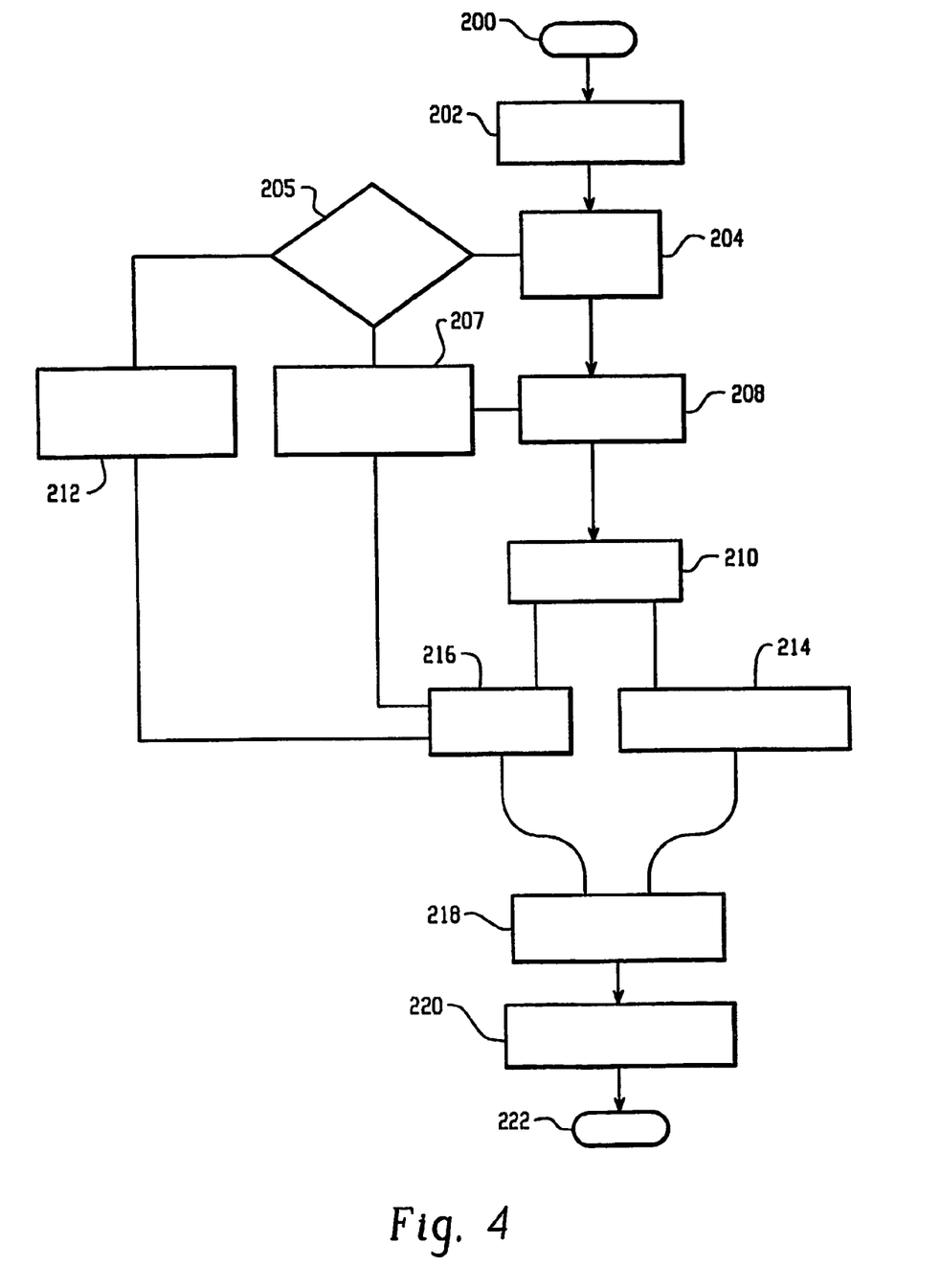
FIG. 4 is a flow diagram illustrating an alternate functional arrangement in accordance with principles of the present invention.

Turning to FIG. 4, an alternate method applying principles of the present invention is illustrated. In step 200, the diagnostic imaging apparatus is initialized and calibrated according to known methods. In step 202, the system parameters for the C-arm system such as positions of components and other conditions necessary for system operation are collected and provided to the system control 26. In step 204, the system acquires the images rotational acquisition and correlated ECG data for each acquired image. The C-arm is placed near the head-position of the table in order to perform a calibrated propeller acquisition from 120 RAO (right side of patient) to 120 LAO (left side of patient). The C-arm rotates with 55 degrees per second and acquires images at 30 frames per second during 4 seconds while the patient holds his/her breath. A total of 8–12 cc's of contrast medium (Omnipaque 350) is injected during the acquisition and started when the gantry starts rotating. This acquisition has been calibrated in step 100 and therefore, the individual projections can be corrected for the earth magnetic field and pincushion distortion and transformed to a common world coordinate system. The projections and the corresponding ECG information is stored in memory for selective recall and display on one of the monitors 24 or 64.

In step 205, the system is adapted to generate both or either of (i) a full volumetric reconstruction in step 212, similar to step 112 above in FIG. 2 and (ii) a cardiac gated volumetric reconstruction of a portion of the arterial tree, for example, including the main branches for the tree which includes the modeled segment of interest. In step 205, if the system is set to generate only the full volumetric reconstruction in step 112, the process is similar to that in FIG. 2. Alternatively, the system may only generate a partial volumetric reconstruction using only images from the same portion of the cardiac cycle, ECG gated images, to generate a more clear partial cardiac arterial tree which includes the modeled segment of interest. In addition, the system may generate both a full volumetric reconstruction using all acquired images which will provide information illustrating aspects of the cardiac motion and generate the partial volumetric reconstruction which includes the modeled segment.

Next, in step 208, a sub-set of the images acquired during the rotational acquisition are displayed on the monitor bank 24 or system monitor 64 for use by the clinician. Based on the ECG signal, the projections that correspond to the same selected phase of the cardiac cycle are chosen to model the segment of the artery of interest as well as provide the images for the partial reconstruction that is generated in step 207. Usually 2 projected images from different angles are selected for the model and all of the images from the same portion of the cardiac cycle, 4–6 gated images in a typical scan in this method, are used for the partial volumetric reconstruction. The modeled segment of interest generated from acquisitions from the same portion of the cardiac cycle provide the necessary accuracy to allow the clinician to mark the displayed image and have accurate measurements generated from the model that can be used for accurate selection of the proper stent or other interventional procedure.

As discussed above for FIG. 2, it is to be appreciated that the entire coronary vascular structure is not modeled. Modeling only the selected segment of interest, e.g. the stenosis or lesion which requires the improved accuracy for the Quantitative Coronary Analysis to be measured for the upcoming interventional procedure, reduces the computational time to construct the necessary maps described below such that the diagnostic process and interventional procedure may be carried out in real time with the patient in the surgical suite.

Once the desired images are selected from the rotational acquisitions, the process moves to step 210 where the model segments are generated. The process in step 210 is similar to that described above for step 110 in FIG. 2.

As mentioned above, in step 112, the volumetric reconstruction is generated. An adapted version of the Feldkamp backprojection algorithm is applied to all of the acquired projections for the volumetric reconstruction. The projections are weighted according to the speed of time C-arm such that the projections acquired at a constant rotation speed have a higher weight than those acquired during startup and slowing down of the C-arm. Since all available projections are used, the reconstruction contains information about several phases of the heart simultaneously, and is often difficult to interpret. Also described above, in step 207, the Feldkamp Backprojection algorithm is applied to only those projections that correspond to the same time point in the cardiac cycle used to build the surface model, the partial reconstructed volume is better suited for simultaneous visualization and inspection of the artery with the modeled segment of interest. The volumetric reconstruction information from steps 207 and/or 212 is provided to step 216.

In step 216, the overlap map is computed as described above for step 116 of FIG. 2 and is carried out by the control console 26. Although the volumetric reconstruction of all the acquired projections yields only a rough representation of the coronaries, it does provide useful information such as the location of the vessels and other objects (e.g. the spine, ribs and pacemaker or ECG-leads) during all the phases of the heart. If the partial reconstruction is included the branch of the coronary arterial tree is more clearly illustrated.

In step 214, the foreshortening map is computed by comparing the length of the modeled segment to the projected length of this segment as if it were viewed from a typical viewpoint as defined by the range of angles in the map.

Next, in step 218, the optimal view map can he constructed by taking a weighted sum of normalized values of the foreshortening map and overlap map. For a practical implementation and efficient computation, the vessel overlap is generally estimated for gantry angles where the vessel foreshortening has been reduced or minimized in order to obtain the resultant optimal working view.

In step 220, the system displays the combined reconstructed image including one or both of the full and/or partial volumetric reconstruction and modeled segment, the optimal view map and system parameters to locate the gantry for a selected optimum view. The images, models and data are displayed on monitors in the monitor bank 24 or the control console 26. The process terminates in step 222.

A hybrid reconstruction scheme including principles of the present invention is described that provides the clinician with three-dimensional quantitative measurement of an accurately modeled arterial segment and an optimal working view throughout the cardiac cycle. This information can be provided in less than a minute and used to plan the intervention while the patient is still on the catheterization table.

While a particular feature of the invention may have been described above with respect to only one of the illustrated embodiments, such features may be combined with one or more other features of other embodiments, as may be desired and advantageous for any given particular application.

From the above description of the invention, those skilled in the art will perceive improvements, changes and modification. For example, other projections captured at the same phase can be used to refine the surface model of the segment of interest. The projections that are approximately of the same phase may be used to visualize the coronary tree, while, all the acquired projections can be used to compute the overlap map. It is to be appreciated that either the full or partial volumetric reconstruction can be used to compute the overlap map or be used to generate images on one of the monitors for visualization of the hybrid coronary 3-D structure. Such improvements, changes and modification within the skill of the art are intended to be covered by the appended claims.

The invention claimed is:

1. A method of generating a hybrid three dimensional reconstruction of a vascular structure affected by periodic motion, the method comprising:
    placing an object affected by periodic motion to be imaged in an imaging region of an x-ray system, the object having a vascular structure;
    acquiring at least two x-ray images of the vascular structure;
    obtaining indicia of the phases of periodic motion and correlating the indicia with each of the at least two x-ray images;
    selecting at least two x-ray images from a similar phase of periodic motion;
    generating a three dimensional modeled segment of a region of interest in the vascular structure, the modeled segment reconstructed using the selected x-ray images from a similar phase of periodic motion, the region of interest only a portion of the imaged vascular structure;
    generating a three dimensional volumetric reconstruction of a vascular structure larger than the modeled segment;
    combining the modeled segment of interest and the volumetric reconstruction of the larger vascular structure; and
    displaying in human readable form the combined reconstructed vascular model and volumetric reconstruction.

2. The method of claim 1 wherein the volumetric reconstruction includes using x-ray images from all of the phases of the periodic motion.

3. The method of claim 1 wherein the volumetric reconstruction is generated with gated images from a similar phase of periodic motion.

4. The method of claim 2 wherein the volumetric reconstruction includes a first portion of the vascular structure reconstructed using x-ray images from all of the phases of periodic motion and a second portion of the vascular structure reconstructed with gated images from a similar phase of the periodic motion.

5. The method of claim 4 wherein the reconstruction of both of the first portion and second portion of the vascular structure are combined with the modeled segment of interest.

6. The method of claim 1 wherein the obtained indicia of phases of periodic motion is representative of cardiac motion and is provided by an ECG signal.

7. The method of claim 1 including computation of an overlap map, the overlap map computed by integrating all the gray values from the reconstructed volume along the rays from a virtual source that intersect the modeled segment located between the virtual source and a virtual image plane.

8. The method of claim 1 wherein acquiring at least two x-ray images of the vascular structure is accomplished with a rotational acquisition using a C-arm x-ray system, the rotational acquisition at an angular velocity of at least 30° per second for a scan period of at least four seconds and less than six seconds.

9. The method of claim 8 wherein the angular velocity is at least 55° during the scan period.

10. An apparatus for generating a hybrid three dimensional reconstruction of a vascular structure affected by periodic motion, the apparatus comprising:
    means for supporting an object affected by periodic motion to be imaged in an imaging region of an x-ray system, the object having a vascular structure;
    means for acquiring at least two x-ray images of the vascular structure;
    means for obtaining indicia of the phases of periodic motion and correlating the indicia with each of the at least two x-ray images;
    means for selecting at least two x-ray images from a similar phase of periodic motion;
    means for generating a three dimensional modeled segment of a region of interest in the vascular structure, the modeled segment reconstructed using the selected x-ray images from a similar phase of periodic motion, the region of interest only a portion of the imaged vascular structure;
    means for generating a three dimensional volumetric reconstruction of a vascular structure larger than the modeled segment;
    means for combining the modeled segment of interest and the volumetric reconstruction of the larger vascular structure; and
    means for displaying in human readable form the combined reconstructed vascular model and volumetric reconstruction.

11. The apparatus of claim 10 wherein the means for volumetric reconstruction uses x-ray images from all of the phases of the periodic motion.

12. The apparatus of claim 10 wherein the means for volumetric reconstruction generates the volumetric reconstruction with gated images from a similar phase of periodic motion.

13. The apparatus of claim 11 wherein the means for volumetric reconstruction includes means for generating a volumetric reconstruction of a first portion of the vascular structure reconstructed using x-ray images from all of the phases of periodic motion and means for generating a volumetric reconstruction for a second portion of the vascular structure with gated images from a similar phase of the periodic motion.

14. The apparatus of claim 13 wherein the means for combining the modeled segment of interest with the volumetric reconstruction includes means for combining both of the first portion and second portion of the vascular structure with the modeled segment of interest.

15. The apparatus of claim 10 including an ECG monitor to obtain the indicia of phases of periodic motion.

16. The apparatus of claim 10 including means for computation of an overlap map, the overlap map computed by integrating all the gray values from the reconstructed volume along the rays from a virtual source that intersect the modeled segment located between the virtual source and a virtual image plane.

17. A method of generating a hybrid three dimensional reconstruction of a vascular structure affected by periodic motion, the method comprising:
    placing an object affected by periodic motion to be imaged in an imaging region of an x-ray system, the object having a vascular structure;
    acquiring a rotational acquisition of x-ray images of the vascular structure;
    obtaining indicia of the phases of periodic motion and correlating the indicia with each of the at least two x-ray images;
    selecting at least two x-ray images from a similar phase of periodic motion;
    generating a three dimensional modeled segment of a region of interest in the vascular structure, the modeled segment reconstructed using the selected x-ray images from a similar phase of periodic motion, the region of interest only a portion of the imaged vascular structure;
    generating a three dimensional volumetric reconstruction of a vascular structure larger than the modeled segment;
    combining the modeled segment of interest and the volumetric reconstruction of the larger vascular structure; and
    displaying in human readable form the combined reconstructed vascular model and volumetric reconstruction.

18. The method of claim 17 wherein the rotational acquisition acquires images at an angular velocity of at least 30° per second for a scan period of at least four seconds and less than six seconds.

19. The method of claim 8 wherein the angular velocity is at least 55° during the scan period.

20. The method of claim 17 wherein the volumetric reconstruction includes using x-ray images from all of the phases of the periodic motion.

21. The method of claim 17 wherein the volumetric reconstruction is generated with gated images from a similar phase of periodic motion.

22. The method of claim 17 wherein the volumetric reconstruction includes a first portion of the vascular structure reconstructed using x-ray images from all of the phases of periodic motion and a second portion of the vascular structure reconstructed with gated images from a similar phase of the periodic motion.

23. The method of claim 22 wherein the reconstruction of both of the first portion and second portion of the vascular structure are combined with the modeled segment of interest.

24. The method of claim 17 wherein the obtained indicia of phases of periodic motion is representative of cardiac motion and is provided by an ECG signal.

25. The method of claim 17 including computation of an overlap map, the overlap map computed by integrating all the gray values from the reconstructed volume along the rays from a virtual source that intersect the modeled segment located between the virtual source and a virtual image plane.

* * * * *